United States Patent [19]
Chan

[11] 3,978,123
[45] Aug. 31, 1976

[54] HERBICIDAL N-ALKYLSULFOXYMETHYL-AND-N-ALKYLSULFONYL-METHYL-N-ARYL UREAS

[75] Inventor: David Cheong King Chan, San Francisco, Calif.

[73] Assignee: Chevron Research Company, San Francisco, Calif.

[22] Filed: Oct. 29, 1974

[21] Appl. No.: 518,665

Related U.S. Application Data

[60] Division of Ser. No. 378,476, July 12, 1973, abandoned, which is a continuation-in-part of Ser. No. 128,563, March 26, 1971, abandoned.

[52] U.S. Cl. .............................. 260/553 A; 71/98; 71/103; 71/120; 260/553 C; 260/553 D
[51] Int. Cl.² ............. C07C 127/15; C07C 127/17; C07C 127/19
[58] Field of Search ......... 260/553 A, 553 D, 553 C

[56] References Cited
UNITED STATES PATENTS

| | | | |
|---|---|---|---|
| 3,060,235 | 10/1962 | Martin et al. | 260/553 A |
| 3,707,557 | 12/1972 | Brown | 260/553 A |
| 3,847,971 | 11/1974 | Koenig et al. | 260/553 A X |

FOREIGN PATENTS OR APPLICATIONS

| | | | |
|---|---|---|---|
| 699,773 | 12/1964 | Canada | 260/553 A |
| 430,323 | 8/1967 | Switzerland | |
| 1,231,952 | 5/1971 | United Kingdom | 260/553 D |
| 1,142,354 | 2/1969 | United Kingdom | 260/553 A |

OTHER PUBLICATIONS
"Isothiocyanates", Klyne et al., CA 62:1585c. (1965).

*Primary Examiner*—Daniel E. Wyman
*Assistant Examiner*—Thomas A. Waltz
*Attorney, Agent, or Firm*—George F. Magdeburger; Dix A. Newell; Raymond Owyang

[57] ABSTRACT

Compounds of the formula

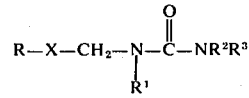

wherein R is alkyl of 1 to 6 carbon atoms or aryl of 6 to 12 carbon atoms substituted with 0 to 5 halogen atoms of atomic number 9 to 35, nitro groups, alkyl groups of 1 to 4 carbon atoms or alkoxy groups of 1 to 4 carbon atoms; one of $R^1$ or $R^2$ is alkyl of 1 to 6 carbon atoms or cycloalkyl of 5 to 6 carbon atoms and the other is aryl of 6 to 12 carbon atoms substituted with 0 to 5 halogen atoms of atomic number 9 to 35, nitro groups, alkyl groups of 1 to 4 carbon atoms or alkyoxy groups of 1 to 4 carbon atoms or trifluoromethyl; $R^3$ is hydrogen or alkyl of 1 to 4 carbon atoms and X is sulfur, SO, $SO_2$ or oxygen, with the proviso that when X is oxygen, $R^1$ is aryl or substituted aryl. The ureas find use as herbicides in both pre- and postemergent applications.

4 Claims, No Drawings

HERBICIDAL N-ALKYLSULFOXYMETHYL-AND-N-ALKYLSULFONYL-METHYL-N-ARYL UREAS

RELATED APPLICATIONS

This application is a division of application Ser. No. 378,476, filed July 12, 1973, now abandoned, which in turn is a continuation-in-part of application Ser. No. 128,563, filed March 26, 1971, the disclosure of which is incorporated herein by reference.

BACKGROUND OF THE INVENTION

1. Field

The present invention is directed to substituted ureas and their use as herbicides. More particularly, the present invention is concerned with methylthiomethyl and methoxymethyl derivatives of N-alkyl-N'-aryl ureas.

2. Prior Art

U.S. Pat. No. 3,125,601 discloses 1-phenyl-3-methoxymethyl-3-methyl ureas and their use as herbicides. See also U.S. Pat. No. 3,148,211, which discloses dialkoxyethyl derivatives of N-alkyl-N'-phenyl ureas in the preparation of herbicidal compositions. Also see U.S. Pat. No. 3,101,370. Netherlands application No. 71/18143, published July 18, 1972, discloses N-substituted-N-trifluoromethylphenyl-N'-methyl ureas.

DESCRIPTION OF THE INVENTION

The compounds of the present invention are represented by the formula

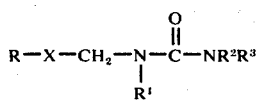

wherein R is alkyl of 1 to 6 carbon atoms or aryl of 6 to 12 carbon atoms substituted with 0 to 5, preferably 0 to 3, more preferably 0 to 2 halogen atoms of atomic number 9 to 35 (fluorine, chlorine or bromine), nitro groups, alkyl groups of 1 to 4 carbon atoms or alkoxy groups of 1 to 4 carbon atoms; one of $R^1$ or $R^2$ is alkyl of 1 to 6 carbon atoms or cycloalkyl of 5 to 6 carbon atoms and the other of $R^1$ or $R^2$ is aryl of 6 to 12 carbon atoms substituted with 0 to 5, preferably 0 to 2 halogen atoms of atomic number 9 to 35, nitro groups, alkyl groups of 1 to 4 carbon atoms, alkoxy groups of 1 to 4 carbon atoms or trifluoromethyl; $R^3$ is hydrogen or alkyl of 1 to 4 carbon atoms and X is $S(O)_n$ wherein n is 0, 1 or 2, or oxygen, with the proviso that when X is oxygen, $R^1$ is substituted aryl.

Preferably R is an alkyl group of 1 to 3 carbon atoms, more preferably methyl, or a phenyl group substituted with from 1 to 2 halogen atoms of atomic number 17 to 35 (chlorine or bromine) preferably chlorophenyl, and $R^1$ or $R^2$, but not both, is an alkyl group of 1 to 4 carbon atoms or cyclohexyl, and the other of $R^1$ or $R^2$ is phenyl containing from 0 to 2 halogen atoms of atomic number 9 to 35 (fluorine, chlorine or bromine), preferably fluorine or chlorine, or trifluoromethyl. Still more preferably, when $R^1$ or $R^2$ is aryl substituted with trifluoromethyl, only one such trifluoromethyl group is present. Preferably $R^3$ is hydrogen or methyl.

The preferred compounds are those wherein $R^1$ is aryl or substituted aryl and $R^2$ is alkyl or cycloalkyl.

While X can be $S(O)_n$ wherein n is 0 to 2 or oxygen, it is preferred that X be $S(O)_n$.

Representative alkyl groups which R, $R^1$ and $R^2$ may represent include methyl, ethyl, n-propyl, isopropyl, n-butyl, isobutyl, sec.butyl, pentyl and hexyl.

Representative aryl groups which $R^1$ and $R^2$ may represent include phenyl, naphthyl, 2-fluorophenyl, 2-chlorophenyl, 2-bromophenyl, 2,4-dichlorophenyl, 2-chloro-1-naphthyl, 2,4-dimethylphenyl, 3-nitrophenyl, 2-nitro-4-chlorophenyl, 2-trifluoromethylphenyl, 3-trifluoromethylphenyl, 2-methoxyphenyl, 2-methoxy-3-chlorophenyl, 4-methoxyphenyl, 4-methylphenyl, 4-butylphenyl, 4-butoxyphenyl, etc.

Another preferred class of compounds is that wherein X is oxygen; R is alkyl of 1 to 6 carbon atoms, preferably 1 to 4 carbon atoms; $R^1$ is phenyl substituted with from 0 to 2 fluorine or chlorine or 0 to 1 trifluoromethyl, preferably 3-trifluoromethyl; $R^2$ is alkyl of 1 to 6 carbon atoms, preferably 1 to 4 carbon atoms; and $R^3$ is hydrogen or alkyl of 1 to 4 carbon atoms.

Still another preferred class of compounds is that wherein X is $S(O)_n$ and n is 0, 1 or 2, preferably 0; R is alkyl of 1 to 6 carbon atoms, preferably 1 to 3 carbon atoms; one or $R^1$ or $R^2$ is alkyl of 1 to 6 carbon atoms and the other of $R^1$ or $R^2$ is phenyl substituted with from 0 to 2 fluorine or chlorine or 0 to 1 trifluoromethyl, preferably 3-trifluoromethyl; and $R^3$ is hydrogen or alkyl of 1 to 4 carbon atoms.

Representative compounds of the present invention include: N-phenyl-N-methylthiomethyl-N'-methyl urea,
N-2-fluorophenyl-N-methylthiomethyl-N'-dimethyl urea,
N-2,4-difluorophenyl-N-methylthiomethyl-N'-ethyl urea,
N-2,4-dichlorophenyl-N-methylthiomethyl-N'-n-butyl urea,
N-2,4-dinitrophenyl-N-methylthiomethyl-N'-methyl urea,
N-4-chlorophenyl-N-methylthiomethyl-N'-methyl urea,
N-4-trifluoromethylphenyl-N-methylthiomethyl-N'-methyl urea,
N-2-methylphenyl-N-methylthiomethyl-N'-methyl urea,
N-2,4-dimethoxyphenyl-N-methylthiomethyl-N'-methyl urea,
N-fluorophenyl-N-phenylthiomethyl-N'-methyl urea,
N-4-fluorophenyl-N-2-chlorophenylthiomethyl-N',N'-dimethyl urea,
N-3,4-dichlorophenyl-N-2,4-dichlorophenylthiomethyl-N'-methyl-N'-n-propyl urea,
N-methylthiomethyl-N-methyl-N'-2,4-dichlorophenyl urea,
N-phenylthiomethyl-N-methyl-N'-2-bromophenyl urea,
N-methylthiomethyl-N-ethyl-N'-2-nitrophenyl urea,
N-methylthiomethyl-N-sec.butyl-N'-3-methoxyphenyl urea,
N-2-fluorophenyl-N-methylsulfoxymethyl-N'-methyl urea,
N-3-chlorophenyl-N-methylsulfonylmethyl-N'-ethyl urea,
N-methylsulfoxymethyl-N-hexyl-N'-3,4-dichlorophenyl urea,
N-methylsulfonylmethyl-N-methyl-N'-2,4-dichlorophenyl urea,
N-2-fluorophenyl-N-methoxymethyl-N'-ethyl urea, N-2,4,6-trifluorophenyl-N-methoxymethyl-N'-methyl urea,
N-2-bromophenyl-N-methoxymethyl-N'-cyclohexyl urea,
N-2,6-dimethylphenyl-N-methoxymethyl-N'-methyl urea,
N-2,6-dimethylphenyl-N-methylthiomethyl-N'-methyl urea,
N-4-phenoxyphenyl-N-methoxymethyl-N'-methyl urea,
N-4-phenoxyphenyl-N-methylthiomethyl-N'-methyl urea, etc.

Compounds wherein X is sulfur are prepared by the reaction of an appropriate N-aryl-N'-alkyl urea with a chloromethyl alkyl sulfide in the presence of a base. The structure of the product depends on the nature of the base. With a strong base, compounds are obtained in which $R^1$ is an aryl group. With a weak base, compounds are obtained in which $R^2$ is the aryl group. Thus, the reactions may be represented as follows:

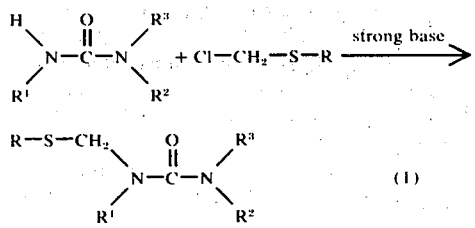

(1)

wherein $R^1$ is an aryl group, $R^2$ is an alkyl or cycloalkyl group, R is as defined above, and $R^3$ is hydrogen;

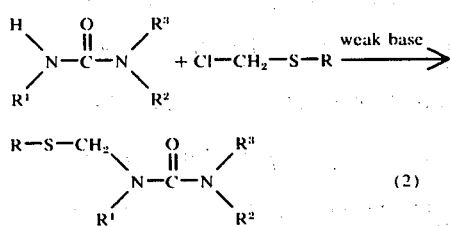

(2)

wherein $R^1$ is an alkyl or cycloalkyl group, $R^2$ is an aryl group, R is as defined above, and $R^3$ is hydrogen. When $R^3$ is alkyl, the substitution occurs at the available hydrogen.

The strong base reactions are carried out at relatively low temperatures, i.e., in the range of 0° to 30°C., and preferably at atmospheric pressure. This reaction is carried out in two steps. In the first step, a molar amount of the strong base is mixed with the urea in a relatively nonpolar solvent. Then, an equivalent or slight excess of chloromethyl alkyl sulfide is added and the resulting mixture is stirred for about 15 or more minutes to insure complete reaction. The relatively nonpolar solvents employed in this reaction include benzene, chloroform, 1,2-dimethoxyethane, etc.

Usually sufficient solvent is used to dissolve the urea feed material, and up to ten times or more of that amount may also be used. The strong bases employed in this reaction include sodium hydride, n-butyl lithium, benzyl potassium, etc. The reaction product may be isolated and purified in any of the usual ways. The preferred method involves evaporation of the solvent and recrystallization of the solid product from an appropriate solvent. Solvents found successful for crystallization of this type of compound include hexane, benzene, diethyl ether, hexane-diethyl ether mixtures, and benzene-hexane mixtures.

The weak base reaction is carried out at moderate temperatures, usually in the range of 20° to 50°C., and preferably at atmospheric pressure. The solvent employed in these reactions is a relatively polar solvent, such as acetone. This reaction is usually carried out by refluxing an equimolar mixture of the urea, chloromethyl alkyl sulfide, and weak base contained in the polar solvent. Reactions are usually completed within 5 to 50 hours. The weak bases employed in this reaction include sodium bicarbonate, potassium bicarbonate, triethyl amine, pyridine, etc. The product isolation and purification are carried out the same as for the strong base reaction product.

Ether analogs cannot be made by the weak-base method, as the product is a bismethylene derivative (see U.S. Pat. No. 3,101,370). However, the strong-base method does work for the ether analog and, therefore, compounds having $R^1$ as an aryl group, $R^2$ as an alkyl or cycloalkyl group, and R and $R^3$ as defined previously, are obtained according to the following equation:

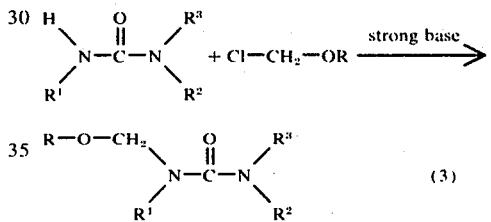

(3)

The strong-base method of preparation of compounds wherein X is oxygen is carried out substantially as described for preparing compounds wherein X represents sulfur.

The ureas employed as feedstocks for the above reactions are well-known compounds and are available from commercial sources or may be prepared by the well-known reactions of an arylamine with an alkyl isocyanate or an alkyl amine with an aryl isocyanate.

The chloromethyl sulfides and ethers used herein are also well-known compounds available from commercial sources. They may be prepared by the reaction of a mercaptan or alcohol with formaldehyde and hydrochloric acid.

The compounds of this invention may also be prepared by another alternate series of reactions. Thus, an appropriate aryl or alkyl or cycloalkyl amine may be reacted with a chloromethyl alkyl sulfide (or ether) and the resulting secondary amine may then be further reacted with an aryl-, alkyl- or cycloalkylisocyanate to give the desired product according to the following reaction:

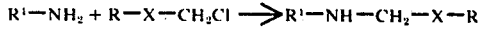

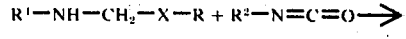

-continued

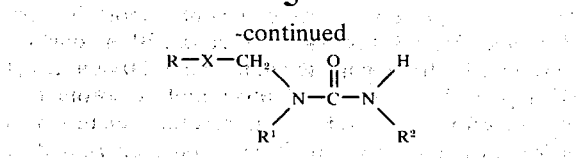

wherein R, R¹, R² and X are as defined above (note that R³ is H). Reaction temperatures will generally be 20° to 35°C., and reaction time will be 5 to 50 hours. Suitable solvents such as dichloromethane or benzene may also be used in an amount from 10 to 50% of the total weight.

The sulfide-type compounds of this invention may be oxidized to the corresponding sulfoxides or sulfones. Oxidation is accomplished by reacting the sulfide with one or two mols of an oxidizing agent to obtain a sulfoxide or sulfone, respectively. Typical oxidizing agents for this reaction are perbenzoic acid, m-chloroperbenzoic acid, peracetic acid, and hydrogen peroxide. The reaction is usually carried out in a solvent such as dichloromethane, chloroform, acetic acid and other inert solvents. The reaction occurs readily at ambient temperatures; cooling means may be necessary for large-sized batches. Reaction time is generally from 2 to 24 hours. The product is worked up by washing with a weak base, such as aqueous sodium bicarbonate, to remove the acid residues, followed by evaporation and recrystallization.

EXAMPLES

The present invention may be more fully understood by reference to the following examples.

EXAMPLE 1

Preparation of N-(2-fluorophenyl)-N-methylthiomethyl-N'-methyl urea

A solution of 16.8 g. (0.1 mol) of N-(2-fluorophenyl)-N'-methyl urea in 250 ml. of 1,2-dimethoxyethane was cooled to 0°C. Then 4.8 g. (0.1 mol) of a 50% dispersion of sodium hydride in mineral oil was added slowly. After addition was complete, the solution was stirred for 15 minutes. This solution was added slowly to a stirred solution of 9.7 g. (0.1 mol) of chloromethyl methyl sulfide in 100 ml. of 1,2-dimethoxyethane. The resulting mixture was stirred at room temperature for 65 hours. At the end of this time, the precipitate was removed by filtration and the resulting filtrate was evaporated to give an oil which solidified upon adding water. The solid was isolated by filtration, washed with hexane and dried. Recrystallization from a hexene-benzene mixture gave 12 g. crystalline solid, melting point 102.5°–103°C. An infrared spectrum showed sharp, strong adsorptions at 3.0, 6.1, 13.05 and 13.2μ.

EXAMPLE 2

Alternate Preparation of N-(2-fluorophenyl)-N-methylthiomethyl-N'-methyl urea o-Fluoroaniline, 22.0 g. (0.2 mol) was dissolved in 30 g. of triethylamine. Then 19.5 g. (0.2 mol) of chloromethyl methyl sulfide was added dropwise. About 10 minutes after all was added, an exothermic reaction occurred and the temperature rose to 93°C. The reaction mixture was allowed to cool to room temperature and then 300 ml. of diethyl ether was added. The resulting solution was washed with 100 ml. of water, dried, and evaporated to give an oil which was chromatographed on 240 g. of silica gel. It was diluted with a 99/1 solution of hexane and diethyl ether. In this way 19.5 g. of crude product was recovered. NMR spectra indicated this to be about 66% N-methylthiomethyl 2-fluoroaniline.

5.0 g. of the crude product were dissolved in 80 ml. of benzene containing 3.0 g. of triethylamine, and then 23 g. of a 12.5% solution of phosgene in benzene was added dropwise. When all was added, the mixture was stirred for about 1 hour more. Then the solid precipitate was removed by filtration. The filtrate was evaporated to give an oily substance.

The oil obtained above (7.0 g.) was dissolved in 150 ml. of benzene, and then gaseous methylamine was bubbled through the stirred solution until there was no more exothermic temperature rise. The mixture was stirred for 2 more hours. After filtering, the filtrate was evaporated to give a solid residue. This residue was crystallized from ethyl ether-hexane and then from diethylether to give 1.0 g. of product, melting point 122°–122.5°C. The infrared spectrum was identical to that of Example 1. Analysis, calculated for $C_{10}H_{13}FN_2OS$: S, 14.03%; F, 8.32%. Found: S, 13.59%; F, 8.51%. An NMR analysis was consistent with the assigned structure.

EXAMPLE 3

Preparation of N-methyl-N-methylthiomethyl-N'-(2-fluorophenyl) urea

To a stirred slurry of 16.8 g. (0.1 mol) of N-(2-fluorophenyl)-N'-methyl urea, dissolved in 500 ml. of acetone containing 9.24 g. (0.11 mol) of sodium bicarbonate was added 10.6 g. ( (0.11 mol) of chloromethyl methyl sulfide. The resulting mixture was stirred for 2 hours at a gentle reflux. The precipitated solid was removed by filtration. The filtrate was evaporated to give a clear oil. Crystallization from benzene gave 7.1 g. of the original urea. The filtrate from this crystallization was evaporated and the residue crystallized from diethylether to give 3.4 g. of a crystalline solid product, melting point 81°–82°C. Analysis calculated for $C_{10}H_{13}FN_2OS$: S, 14.03%; F, 8.32%. Found: S, 14.02%; F, 8.43%. The infrared spectrum showed strong adsorption at 3.0, 6.9, 7.3 and 13.0μ. The NMR spectra was consistent with the assigned structure.

EXAMPLE 4

Preparation of N-(2-fluorophenyl)-N-methoxymethyl-N'-methyl urea

To a stirred solution of 8.4 g. (0.05 mol) of N-(2-fluorophenyl)-N'-methyl urea dissolved in 200 ml. of 1,2-dimethoxyethane there was added 2.4 g. of a 50% dispersion of sodium hydride (0.05 mol) in mineral oil. The resulting mixture was stirred for 15 minutes more. Then 4.2 g. (0.05 mol) of chloromethyl methyl ether was added dropwise. After all ether was added, the mixture was stirred for 16 hours. At the end of this time it was filtered through a layer of magnesium sulfate. The filtrate was evaporated to give an oily residue which crystallized upon standing. These crystals were washed with hexane and then dried to give 6.2 g. of product, melting point 57°–59°C. Analysis: Calculated for $C_{10}H_{13}FN_2O_2$: F, 8.96%; Found: F, 8.97%. The infrared spectrum showed strong adsorptions at 6.1, 6.6, 6.7, 6.9, 7.8, 9.1 and 13.5μ. The NMR spectra was consistent with the assigned structure.

EXAMPLE 5

Preparation of N-(3,4-dichlorophenyl)-N-methylsulfoxymethyl-N'-methyl urea

N-(3,4-dichlorophenyl)-N-methylthiomethyl-N'-methyl urea, 3.0 g. (0.01 mol) was dissolved in 75 ml. of dichloromethane. Then 2.3 g. (0.013 mol) of m-chloroperbenzoic acid was added in small portions. The reaction mixture was allowed to stand for 65 hours. An aqueous sodium bicarbonate solution was added and after thorough contact, the organic layer was separated, washed with water and dried. Upon evaporation of the solvent an oil was obtained which was chromatographed on 70 g. of silica gel. The product, 2.5 g., was eluted with a 50/50 mixture of acetone-diethyl ether. Analysis, calculated for $C_{10}H_{12}Cl_2N_2O_2S$: Cl, 24.0%; S, 10.83%. Found, Cl, 25.9%; S, 10.03%. The infrared spectrum had a strong adsorption at 1020 cm$^{-1}$, characteristic of a sulfoxy compound.

EXAMPLE 6

Preparation of N-(2-fluorophenyl)-N-methylsulfonylmethyl-N'-methyl urea

N-(2-fluorophenyl)-N-methylthiomethyl-N'-methyl urea (prepared as in Example 1), 6.3 g. (0.0275 mol) was dissolved in 500 ml. of dichloromethane. Then 10.4 g. (0.055 mol) of m-chloroperbenzoic acid was added in small portions. The resulting mixture was allowed to stand for 16 hours at ambient temperature. At the end of this time the solution was washed first with 300 ml. of water containing 10 g. of sodium bicarbonate and then with water. After drying, the solvent was removed by evaporation. The resulting solid was recrystallized from a dichloromethane-diethyl ether mixture to give 4.0 g. of crystalline product, melting point 168°–170°C. Analysis, calculated for $C_{10}H_{13}FN_2O_3S$: F, 7.30%; S, 12.3%. Found: F, 7.54%; S, 12.60%. The infrared spectrum had strong adsorption bands at 7.7$\mu$ and 8.7$\mu$, characteristic of the sulfonyl group. The NMR spectrum was consistent with the assigned structure.

EXAMPLE 7

Preparation of N-methyl-N'-methoxymethyl-N'-3-trifluoromethylphenyl urea

A 3.5-g (0.0685 mol NaH) sample of 50% sodium hydride mineral oil dispersion was added in small portions to a solution of 15 g. (0.0685 mol) N-3-trifluromethylphenyl-N'-methyl urea in 250 ml dimethoxyethane. After complete addition, the mixture was stirred for 20 minutes. A 5.7 g. (0.0685 mol) sample of chloromethyl methyl ether was added. A mild exotherm ensued. The reaction mixture was stirred at about 25°C. for 2 days. The solid contents of the reaction mixture were filtered through a layer of magnesium sulfate and washed with methylene dichloride. The filtrate was evaporated under reduced pressure to give an oil. The oil was chromatographed on silica gel (200 g.). Elution with 50% hexane/ether gave the product as a pale yellow oil. Elemental analysis for $C_{11}H_{13}F_3N_2O_2$ showed: %F, calculated 21.72; found 21.75.

EXAMPLE 8

Preparation of N-methyl-N'-methylthiomethyl-N'-3-trifluoromethylphenyl urea

A 3.5 g. (0.0685 mol NaH) sample of 50% sodium hydride mineral oil dispersion was added in small portions to a solution of 15 g. (0.0685 mol) N-3-trifluoromethylphenyl-N'-methyl urea in 250 ml. dimethoxyethane. After complete addition and 20 minutes of stirring at 25°C., 6.7 g. (0.0685 mol) chloromethyl methyl sulfide was added. The reaction mixture was stirred at about 25°C. for 2 days and then heated at reflux for about 5 hours. After standing overnight at about 25°C., the solid contents were filtered through a layer of magnesium sulfate and washed with methylene dichloride. The filtrate was evaporated under reduced pressure to give an oil. The oil was chromatographed on silica gel (200 g.) Elution with 50% hexane/ether gave the product as a white solid, melting point 64°–67°C. Elemental analysis for $C_{11}H_{13}F_3N_2OS$ showed: %F, calculated 20.43, found 20.41; %S, calculated 11.49; found 11.61.

EXAMPLE 9

Preparation of N-3-trifluoromethylphenyl-N'-methyl-N'-methylthiomethyl urea

A 6.7 g. (0.0687 mol) sample of chloromethyl methyl sulfide was added to a solution of 15.0 g. (0.0687 mol) N-3-trifluoromethylphenyl-N'-methyl urea and 7.4 g. 2,6-lutidine in 500 ml. acetone. The reaction mixture was heated at reflux for 22 hours. After cooling to about 25°C., the reaction mixture was filtered. The filtrate was evaporated under reduced pressure and the resulting oil was chromatographed on silica gel (200 g.) The chromatography failed to produce a pure product. The combined chromatography fractions were therefore combined in methylene dichloride, washed with 10% aqueous hydrochloric acid, dried over magnesium sulfate and evaporated under reduced pressure to give and oil. Crystallization of the oil from hexane gave the product as a pale yellow solid, melting point 65°–67°C. Elemental analysis for $C_{11}H_{13}F_3N_2OS$ showed: %S, calculated 11.49, found 11.68; %F, calculated 20.43, found, 21.33.

Other compounds were also prepared using the methods as described above. These compounds are listed in Table I.

UTILITY

The ureas of the present invention are, in general, herbicidal in both pre- and post-emergent applications. For pre-emergent control of undesirable vegetation, these ureas will be applied in herbicidal quantities to the environment, e.g., soil infested with seeds and/or seedlings of such vegetation. Such application will inhibit the growth of or kill the seeds, germinating seeds and seedlings. For post-emergent applications, the ureas of the present invention will be applied directly to the foliage and other plant parts. Generally they are effective against weed grasses as well as broadleaved weeds. Some may be selective with respect to type of application and/or type of weed.

Pre- and post-emergent herbicidal tests on representative ureas of this invention were made using the following methods:

PRE-EMERGENT TEST

An acetone solution of the test ureas was prepared by mixing 750 mg. urea, 220 mg. of a nonionic surfactant and 25 ml. of acetone. This solution was added to approximately 125 ml. of water containing 156 mg. of surfactant.

Seeds of the test vegetation were planted in a pot of soil and the urea solution was sprayed uniformly onto the soil surface at a dose of 100 mg. per cm². The pot was watered and placed in a greenhouse. The pot was watered intermittently and was observed for seedling emergence, health of emerging seedlings, etc., for a 3-week period. At the end of this period the herbicidal effectiveness of the urea was rated based on the physiological observations. A 0 to 100 scale was used, 0 representing no phytotoxicity, and 100 representing complete kill.

POST-EMERGENT TEST

The test urea was formulated in the same manner as described above for the pre-emergent test. The concentration of the urea in this formulation was 5000 ppm. This formulation was uniformly sprayed on 2 similar pots of 24-day-old plants (approximately 15 to 25 plants per pot) at a dose of 100 mg. per cm². After the plants had dried, they were placed in a greenhouse and then watered intermittently at their bases as needed. The plants were observed periodically for phytotoxic effects and physiological and morphological responses to the treatment. After 3 weeks the herbicidal effectiveness of the urea was rated based on these observations. A 0 to 100 scale was used, 0 representing no phytotoxicity, 100 representing complete kill.

The results of these tests appear in Table II.

TABLE I

| Compound | m.p., °C. | Calculated Halogen | Calculated S | Found Halogen | Found S |
|---|---|---|---|---|---|
| N-3,4-dichlorophenyl-N-methylthiomethyl-N'-methyl urea | 103–105 | 25.42 | 12.59 | 25.55 | 11.35 |
| N-2-fluorophenyl-N-methylthiomethyl-N',N'-dimethyl urea | Oil | 7.84 | 13.21 | 7.73 | 12.20 |
| N-4-chlorophenyl-N-methylthiomethyl-N'-methyl urea | 71.5–72.5 | 14.5 | 13.05 | 15.12 | 12.52 |
| N-4-chlorophenyl-N-methylthiomethyl-N'-isopropyl urea | 69–69.5 | 7.41 | 12.5 | 8.37 | 10.88 |
| N-2-fluorophenyl-N-methylthiomethyl-N'-cyclohexyl urea | 60–61.5 | 6.41 | 10.78 | 6.49 | 10.47 |
| N-3-chlorophenyl-N-methylthiomethyl-N'-methyl urea | 86.5–87.5 | 14.5 | 13.05 | 14.8 | 12.78 |
| N-3-trifluoromethylphenyl-N-methylthiomethyl-N'-methyl urea | 64–67 | 20.43 | 11.49 | 20.41 | 11.61 |
| N-2-fluorophenyl-N-methylthiomethyl-N'-n-butyl urea | 70–71 | 7.03 | 11.82 | 7.36 | 11.42 |
| N-2-fluorophenyl-N-methylthiomethyl-N'-isobutyl urea | 87–89 | 7.03 | 11.82 | 7.35 | 11.28 |
| N-2-fluorophenyl-N-methylthiomethyl-N'-sec.butyl urea | 35–36 | 7.03 | 11.82 | 7.24 | 11.60 |
| N-4-chlorophenyl-N-methyoxymethyl-N'-methyl urea | 83–83.5 | 15.5 | 12.2* | 14.2 | 11.2* |
| N-2-trifluoromethylphenyl-N-methoxymethyl-N'-methyl urea | Oil | 21.72 | — | 21.75 | — |
| N-2-fluorophenyl-N-methoxymethyl-N',N-dimethyl urea | Oil | 8.40 | — | 8.65 | — |
| N-2-fluorophenyl-N-4-chlorophenylthiomethyl-N'-methyl urea | 98–101 | 10.9 | 9.85 | 9.7 | 8.51 |
| N-3,4-dichlorophenyl-N-methyoxymethyl-N'-methyl urea | 81–82.5 | 27.0 | 10.63* | 26.80 | 9.92* |
| N-2-fluorophenyl-N-phenylthiomethyl-N',N'-dimethyl urea | Oil | 6.24 | 10.51 | 6.49 | 10.78 |
| N-methylthiomethyl-N-methyl-N'-3,4-dichlorophenyl urea | 96–98 | 25.42 | 12.59 | 25.20 | 11.64 |
| N-methylthiomethyl-N-methyl-N'-4-chlorophenyl urea | 117–117.5 | 14.5 | 13.05 | 14.62 | 12.99 |
| N-methylthiomethyl-N-methyl-N'-3-trifluoromethylphenyl urea | 65–67 | 20.43 | 11.49 | 21.33 | 11.68 |
| N-methylthiomethyl-N-methyl-N'-3-chlorophenyl urea | 73–78 | 14.5 | 13.05 | 14.75 | 12.91 |
| N-4-chlorophenylthiomethyl-N-methyl-N'-2-fluorophenyl urea | 74–75 | 10.92 | 9.85 | 10.71 | 9.87 |

*Nitrogen analysis

TABLE II

| Compound | Herbicidal Effectiveness Pre/Post O | W | C | M | P | L |
|---|---|---|---|---|---|---|
| N-2-fluorophenyl-N-methylthiomethyl-N'-methyl urea | 100/100 | 100/100 | 100/100 | 100/100 | 100/100 | 100/100 |
| N-3,4-dichlorophenyl-N-methylthiomethyl-N'-methyl urea | 90/100 | 100/100 | 100/100 | 100/100 | 100/100 | 100/100 |
| N-2-fluorophenyl-N-methylthiomethyl-N',N'-dimethyl urea | 80/– | — | 90/– | 100/100 | 100/100 | 100/100 |
| N-4-chlorophenyl-N-methylthiomethyl-N'-methyl urea | 100/90 | 100/90 | 95/– | 100/90 | 100/– | 100/– |
| N-4-chlorophenyl-N-methylthiomethyl-N'-isopropyl urea | 100/100 | 100/95 | 100/95 | 100/100 | 100/100 | 100/100 |
| N-2-fluorophenyl-N-methylthiomethyl-N'-cyclohexyl urea | 75/– | 80/– | 85/– | 90/– | — | 100/– |
| N-3-chlorophenyl-N-methylthiomethyl-N'-methyl urea | 100/– | 100/– | 100/– | 100/90 | 100/85 | 100/85 |
| N-3-trifluoromethylphenyl-N-methylthiomethyl-N'-methyl urea | 95/95 | 97/98 | 97/78 | 98/100 | 93/– | 100/99 |
| N-2-fluorophenyl-N-methylthiomethyl-N'-n-butyl urea | 95/100 | 100/100 | 100/100 | 100/100 | 100/90 | 100/100 |
| N-2-fluorophenyl-N-methylthiomethyl-N'-isobutyl urea | — | 80/– | — | 85/– | — | 75/– |
| N-2-fluorophenyl-N-methylthiomethyl-N'-sec.butyl urea | 75/100 | 100/95 | 100/95 | 100/100 | 100/90 | 100/100 |
| N-2-fluorophenyl-N-methoxymethyl-N'-methyl urea | 100/100 | 100/100 | 100/100 | 100/100 | 100/100 | 100/100 |
| N-4-chlorophenyl-N-methoxymethyl-N'-methyl urea | 100/95 | 100/90 | 100/90 | 100/100 | 100/100 | 100/100 |
| N-2-trifluoromethylphenyl-N-methoxymethyl-N'-methyl urea | 88/100 | 100/95 | 100/75 | 99/100 | 83/– | 99/100 |
| N-2-fluorophenyl-N-methoxymethyl-N'-N'-dimethyl urea | — | 95/– | — | 95/100 | 90/100 | 90/100 |
| N-3,4-dichlorophenyl-N-methoxymethyl-N'-methyl urea | 100/100 | 100/100 | 100/100 | 100/100 | 100/100 | 100/100 |
| N-2-fluorophenyl-N-4-chlorophenylthiomethyl-N'-methyl urea | 100/100 | 100/100 | 100/100 | 100/100 | 100/100 | 100/100 |
| N-2-fluorophenyl-N-phenylthiomethyl-N',N'-dimethyl urea | 100/– | 100/90 | 100/– | 100/100 | 100/100 | 100/100 |
| N-methylthiomethyl-N'-methyl-N'-2-fluorophenyl urea | 97/100 | 100/100 | 100/100 | 100/– | 100/100 | 100/100 |
| N-methylthiomethyl-N-methyl-N'-3,4-dichlorophenyl urea | 90/100 | 100/100 | 100/100 | 100/100 | 100/100 | 100/100 |
| N-methylthiomethyl-N-methyl-N'-4-chlorophenyl urea | 100/– | 100/– | 100/– | 100/100 | 100/100 | 100/100 |
| N-methylthiomethyl-N-methyl-N'-3-trifluoromethylphenyl urea | 100/– | 100/– | 100/– | 100/100 | 100/– | 100/– |
| N-methylthiomethyl-N-methyl-N'-3-chlorophenyl urea | 90/– | 90/– | 90/– | 100/– | 95/– | 95/– |
| N-4-chlorophenylthiomethyl-N-methyl-N'-2-fluorophenyl urea | 100/100 | 99/100 | 100/90 | 99/100 | 100/99 | 100/100 |
| N-3,4-dichlorophenyl-N-methylsulfoxymethyl-N'-methyl urea | 90/100 | 100/100 | 100/100 | 99/100 | 95/100 | 95/100 |

TABLE II-continued

| Compound | Herbicidal Effectiveness Pre/Post | | | | | |
|---|---|---|---|---|---|---|
| | O | W | C | M | P | L |
| N-2-fluorophenyl-N-methylsulfonylmethyl-N'-methyl urea | 100/- | 100/- | 100/- | 100/78 | 100/- | 100/90 |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

The amount of urea administered will vary with the particular plant part or plant growth medium which is to be contacted, the general location of application, i.e., sheltered areas such as greenhouses as compared to exposed areas such as fields, as well as the desired type of control. For pre-emergent control of most plants, dosages in the range of about 0.5 to 20 lbs. per acre will be used. Such administration will give a concentration of about 2 to 80 ppm. urea distributed throughout 0.1 acre-foot. For post-emergent application, such as foliar spray application, compositions containing about 0.5 to 8 lbs. urea per 100 gal. spray will be used. Such application is equivalent to about 0.5 to 20 lbs. urea per acre.

The herbicidal compositions of this invention comprise a herbicidal amount of one or more of the above describedureas intimately admixed with a biologically inert carrier. The carrier may be a liquid diluent such as water or acetone or a solid. The solid may be in the form of dust powder or granules. These compositions will also usually contain adjuvants such as a wetting or dispersing agent to facilitate their penetration into the plant growth medium or plant tissue and generally enhance their effectiveness. These compositions may also contain other pesticides, stabilizers, conditioners, fillers and the like.

What is claimed is:

1. A compound of the formula

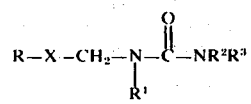

wherein R is alkyl of 1 to 6 carbon atoms, $R^1$ is phenyl substituted with from 0 to 2 fluorine or chlorine or 0 to 1 trifluoromethyl, $R^2$ is alkyl of 1 to 6 carbon atoms, $R^3$ is hydrogen or alkyl of 1 to 4 carbon atoms, and X is $S(O)_n$ wherein $n$ is 1 or 2.

2. The compound of claim 1 wherein $R^3$ is hydrogen.

3. The compound of claim 2 whererin R is methyl, $R^1$ is N-3,4-dichlorophenyl, $R^2$ is methyl and $n$ is 1.

4. The compound of claim 2 wherein R is methyl, $R^1$ is N-2-fluorophenyl, $R^2$ is methyl and $n$ is 2.

* * * * *